DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED FEBRUARY 5, 1974

920 O.G. 9

T919,001
MIXED ACETALS AND PROCESS FOR THEIR PREPARATION

Lucien Person, Chicago, Ill.
(136 Boulevard Jean Jaures, 92-Clichy, France)

Continuation of abandoned application Ser. No. 876,022, No. 12, 1969. This application Dec. 29, 1972, Ser. No. 319,325

**Int. Cl. C07c *43/20***
U.S. Cl. 260—615 B
No Drawing. 16 Pages Specification

Mixed acetals of low molecular weight alcohols and compounds containing one or more hydroxyl groups are prepared by reacting an alpha-halo dialkyl ether, a compound containing at least one hydroxy group and an alkylene oxide in a temperature range of about 20° C. to 150° C. The mixed acetals are useful as surfactants and are characterized by excellent stability in alkaline media.